United States Patent [19]

Blaine et al.

[11] Patent Number: 4,510,322

[45] Date of Patent: Apr. 9, 1985

[54] INDACRINONE HAVING ENHANCED URICOSURIC

[75] Inventors: Edward H. Blaine, Chalfont; Edward J. Cragoe, Jr., Lansdale; Ralph F. Hirschmann, Blue Bell; John F. Nancarrow, deceased, late of Montgomery County; by Elisabeth M. Nancarrow, executrix, Wyndmoor, all of Pa.; Jonathan A. Tobert, New York, N.Y.

[73] Assignee: Merck & Co., Inc., Rahway, N.J.

[21] Appl. No.: 463,685

[22] Filed: Feb. 3, 1983

Related U.S. Application Data

[63] Continuation-in-part of Ser. No. 282,360, Jul. 13, 1981, abandoned, which is a continuation-in-part of Ser. No. 244,508, Mar. 16, 1981, abandoned.

[51] Int. Cl.³ .............................................. C07C 59/80
[52] U.S. Cl. ...................................... 514/255; 562/462; 514/423; 514/569; 514/870
[58] Field of Search ......................... 562/462; 424/262

[56] References Cited

U.S. PATENT DOCUMENTS

| | | | |
|---|---|---|---|
| 3,313,813 | 4/1967 | Cragoe et al. | 260/250 |
| 4,087,542 | 5/1978 | Cragoe et al. | 424/275 |
| 4,096,267 | 6/1978 | Cragoe et al. | 424/262 |
| 4,374,829 | 2/1983 | Harris et al. | 424/177 |

FOREIGN PATENT DOCUMENTS 1475177  6/1977  United Kingdom.

OTHER PUBLICATIONS

Irvin et al., Clin. Pharmacol. Ther., p. 260, (Feb. 1980).
deSolms et al., J. Med. Chem., 21, (No. 5), 437–443, (1978).
Woltersdorf et al., ACS Symposium Series No. 83, *Diuretic* Agents, pp. 219–220, (1978).
Tobert et al., Clin. Pharmacol. Ther., p. 343, (Mar. 1981).
Woltersdorf Jr., Otto–Journal of Labelled Compounds and Radio pharmaceuticals, Vol. XVII, No. 5, 6/12/1979, pp. 635–639.
Chem. Abst., vol. 93, No. 15.

*Primary Examiner*—Paul J. Killos
*Attorney, Agent, or Firm*—Alice O. Robertson; Raymond M. Speer; Michael C. Sudol

[57] ABSTRACT

The uricosuric and diuretic properties of indacrinone, [6,7-dichloro-2,3-dihydro-2-methyl-1-oxo-2-phenyl-1H-inden-5-yl)oxy]acetic acid, are carefully balanced for maximum therapeutic benefit by manipulation of the proportion of (+) and (−) enantiomers in the final product within critical limits.

13 Claims, No Drawings

INDACRINONE HAVING ENHANCED URICOSURIC

This application is a continuation-in-part of copending application, Ser. No. 282,360, filed July 13, 1981, now abandoned, which in turn is a continuation-in-part of copending application, Ser. No. 244,508, filed Mar. 16, 1981, now abandoned.

BACKGROUND OF THE INVENTION

1. Field of the Invention

The present invention is concerned with balancing the uricosuric and diuretic properties of indacrinone, a racemic compound, through manipulation of the proportion of its (+) and (−) enantiomers.

There continues to be a great deal of interest in the discovery and development of diuretics which are also uricosuric, since nearly all currently available diuretics commonly lead to urate retention, hyperuricemia, and, occasionally, attacks of gout. Hyperuricemia, in turn, may itself be a risk factor for the development of cardiovascular disease, carbohydrate intolerance, and urate-induced nephropathy. A large percentage of hypertensive patients have hyperuricemia.

For example, ticrynafen, or tienilic acid, produces a prompt diuresis with an increased excretion of sodium and chloride, while at maximal drug effect, uric acid clearance increases about five-fold. This drug was approved for use as an antihypertensive agent in the United States in 1979, but it was later withdrawn when postmarketing surveillance revealed an unacceptably high incidence of hepatotoxicity.

Uric acid transport by the renal tubules involves both readsorptive and secretory processes. There has been an interest in the mechanism of action of drugs that directly influence tubular transport systems for uric acid and thus alter the rate of uric acid excretion. Probenecid, for example, increases the urinary excretion of uric acid by inhibition of carrier-mediated reabsorption. Likewise, indacrinone or indacrynic acid, utilized in the present invention, inhibits urate reabsorption in the proximal tubule.

The action of uricosuric agents is often seemingly contradictory, because of the complexity of the transport mechanisms involved. Thus, increase, decrease, or lack of effect on the excretion of uric acid is not only highly species dependent, but dosage dependent as well. Moreover, depending on the exact conditions, the combined effect of two uricosuric drugs may be either additive or antagonistic.

The renal transport of uric acid in mammals involves both secretion and reabsorption, but in man the process of reabsorption dominates so that the amount that is excreted is but a small fraction of that which is filtered. A variety of factors, including uricosuric drugs, can influence the relative importance of these bidirectional transport mechanisms in man. Also, as already indicated above, uric acid is transported by carrier-mediated mechanisms and not by diffusion, and in man the site of transport is located in the proximal tubule, including both the convoluted and straight portions.

2. Brief Description of the Prior Art

Indacrinone, as a racemic mixture, and as the (+) or (−) enantiomer, is described in U.S. Pat. No. 4,096,267, which also refers generally to the possibility of combining different indanones disclosed where greater diuretic activity and greater uricosuric activity are possessed by said indanones. However, nothing in this reference would suggest manipulation of the proportion of (+) and (−) enantiomers of indacrinone within critical limits, for careful balancing of uricosuric and diuretic properties to give maximum therapeutic benefit, which has been accomplished with the present invention.

The different pharmacodynamic effects of the (+) and (−) enantiomers of indacrinone, specifically that the principal saluretic activity of indacrinone resides in the (−) enantiomer while uricosuric activity is present in both (−) and (+) enantiomers, are described by Irvin et al., *Clin. Pharmacol. Ther.*, p. 260 (Feb. 1980); de-Solms et al., *J. Med. Chem.*, Vol. 21, No. 5, pp. 437–443 (1978); and Woltersdorf et al. *ACS Symposium Series No. 83 Diuretic Agents*, pp. 219–220 (1978). However, none of these publications in any way suggest manipulation of the proportion of (+) and (−) enantiomers of indacrinone within critical limits so as to achieve the maximum therapeutic benefit from balanced uricosuric and diuretic properties, as is the case with the present invention.

British Pat. No. 1,475,177 describes the combination of indacrinone racemic mixture, or the (−) enantiomer of indacrinone, with a potassium-sparing pyrazinoylguanidine diuretic, especially amiloride. However, this patent does not disclose or suggest a manipulated proportion of (+) and (−) enantiomers of indacrinone, or the combination of such a manipulated proportion with amiloride or other pyrazinoylguanidine diuretics.

U.S. Pat. No. 4,087,542 describes the diuretic (+) isomer and uricosuric (−) isomer of 6,7-dichloro-2,3-dihydro-5-(2-thenoyl)benzofuran-2-carboxylic acid and teaches manipulating the ratio of these isomers to achieve a balance of diuretic and uricosuric properties. However, there is a total separation of diuretic and uricosuric activity between the two isomers, and the manipulation of these isomers would not be instructive as to even the possibility of manipulating the (+) and (−) enantiomers of indacrinone, a wholly different compound. Furthermore, at present there is not known to be any marketed or experimental drug in which a ratio of enantiomers other than the synthetically occurring 50:50 is used.

DETAILED DESCRIPTION OF THE INVENTION AND PREFERRED EMBODIMENTS

Indacrinone, or indacrynic acid, is a potent, high ceiling diuretic which may be renamed as [6,7-dichloro-2,3-dihydro-2-methyl-1-oxo-2-phenyl-1H-inden-5-yl)oxy]acetic acid and may be represented by the following formulas:

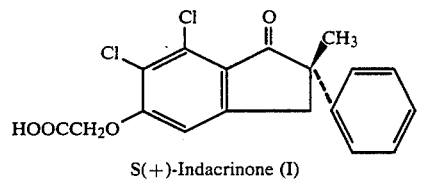

S(+)-Indacrinone (I)

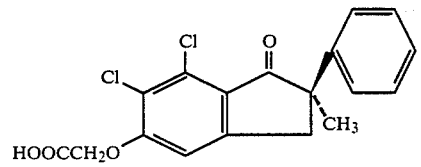

-continued

R(−)-Indacrinone (I)

The compound is a racemic mixture, and methods for its preparation are described in U.S. Pat. No. 4,096,267. Methods for resolving the racemic mixture into its (+) and (−) enantiomers are described in said patent, as well as in deSolms et al., *J. Med. Chem.*, Vol. 21, No. 5, pp. 437–443 (1978).

As will be appreciated, diuretics are valuable therapeutic agents useful in the treatment of cardiovascular and renal diseases, for example in the management of all types and grades of severity of congestive heart failure and in the treatment of mild, moderate, and severe forms of hypertension. As a result of the loss of water and electrolyte, dramatic improvement is noted in peripheral and pulmonary edema, dyspnea, orthopnea, ascites and pleural effusion. Diuretics also provide effective therapy in various forms of renal edema, for example, edema associated with nephrosis and certain types of nephritis. Their administration results in prompt excretion of retained fluid and electrolytes, especially sodium chloride.

In addition to its potent diuretic and saluretic properties, indacrinone also possesses important uricosuric properties as well. However, this uricosuric activity presents a complex picture, as will be apparent from the following.

(1) Both enantiomers of indacrinone possess uricosuric activity. However, the (−) enantiomer, which is 20 to 40 times more potent than the (+) enantiomer as a natriuretic agent, possesses uricosuric activity on an acute basis, that is, within the first few hours of administration, but on a chronic basis, produces hyperuricemia. The uricosuric activity seen on an acute basis is considered to result from the increased flow of water through the renal tubule produced by the (−) enantiomer, together with somewhat decreased reabsorption of urate produced by blockade of that reabsorption by the (−) enantiomer. However, as the acute phase passes and administration of the (−) enantiomer becomes chronic, a decrease in the extracellular fluid volume results which produces a significantly enhanced rate of urate reabsorption. Thus, as the extracellular fluid volume becomes depleted, uricosuria ceases and urate reabsorption increases to the point that hyperuricemia results.

Both the (−) and (+) enantiomers have significant intrinsic uricosuric activity; and it seems probable that they both act on the same site or sites in the proximal portion of the renal tubule which regulate urate reabsorption. When the (−) enantiomer is administered by itself, or when a racemic mixture of (−) and (+) enantiomers is administered, the final result, or net effect will be hyperuricemia, since the higher natriuretic potency of the (−) enantiomer overcomes the urate reabsorption inhibitory potency of both the (−) and (+) enantiomers through the mechanism of extracellular fluid depletion, as explained above.

(2) Both enantiomers of indacrinone possess natriuretic properties. As already described above, the (−) enantiomer is significantly more potent as a natriuretic agent than the (+) enantiomer. However, the (+) enantiomer does have modest potency as a natriuretic agent, which again, further complicates the problem of manipulating the proportion of (+) and (−) enantiomers in order to achieve a balance of diuretic and uricosuric properties.

(3) There is no practical way of reliably associating the degree of extracellular fluid volume depletion, which leads to hyperuricemia, with the extent of urate reabsorption inhibition, which results in uricosuria.

(4) The (+) enantiomer is considered to have a different site of action in the renal tubule from that of the (−) enantiomer, with correspondingly different therapeutic effects. (These sites of action and therapeutic effects are to be distinguished from the urate reabsorption regulation which occurs in the proximal renal tubule for both enantiomers, as already explained above.) The natriuretic activity of the (−) enantiomer is considered to be effected in the ascending limb of Henle's loop portion of the renal tubule. The (+) enantiomer, on the other hand, probably expresses its therapeutic effects in a more distal portion of the renal tubule.

(5) Uricosuric activity is only desirable in the context of avoiding hyperuricemia and its consequences. Since there is no known advantage to a hypouricemic state, and since extensive uricosuria has occasionally cause urate precipitation in renal tubules, the goal of manipulating the proportion of (+) and (−) enantiomers must be to achieve, as nearly as possible, an isouricemic or slightly hypouricemic state, that is, administration of the indacrinone final product should result in neither a rise nor a large fall in patient serum uric acid levels.

As used in this context, the term "slightly hypouricemic" is intended to describe a decrease in serum or plasma uric acid levels of 20% or less from the starting level for a particular patient, or from the mean starting level for a group of patients. The starting level may be a "normal" level or uric acid or it may be a "hyperuricemic" level. It is important to avoid hypouricemia of a greater extent than that indicated, since it is thought that it can result in acute renal failure caused by tubular urate precipitation. Thus, use of ticrynafen can cause a decrease in plasma uric acid levels of as high as 40%, which is considered undesirably high.

Thus, the present invention surprisingly is able to provide potent diuretic and saluretic action together with uricosuric action which achieves a isouricemic or slightly hypouricemic result in human beings, through the use of an unexpectedly narrow range of component ratios for the enantiomers of indacrinone.

Accordingly, the present invention provides a composition of matter comprising in combination, (a) the (+) enantiomer of indacrinone; and
(b) the (−) enantiomer of indacrinone;

wherein the weight ratio of (a):(b) is from 8:1 to 10:1, that is, the (+) enantiomer is from about 89% to 91% by weight of the total, and the (−) enantiomer is correspondingly from 11% to 9% by weight of the total weight of indacrinone.

The preferred ratio of (a):(b) is 9:1, that is, the (+) enantiomer is 90% by weight and the (−) enantiomer is 10% by weight of the total weight of indacrinone.

The present invention also provides a pharmaceutical composition useful in the treatment of edema and hypertension which is also isouricemic or slightly hypouricemic, comprising a therapeutically effective amount of, in combination, (a) the (+) enantiomer of indacrinone; and
(b) the (−) enantiomer of indacrinone;

wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with a non-toxic pharmaceutical carrier.

The present invention further provides a method of treating edema, hypertension, and hyperuricemia, comprising the administration to a patient in need of such treatment of a therapeutically effective amount of, in combination, (a) the (+) enantiomer of indacrinone; and
(b) the (−) enantiomer of indacrinone;

wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone.

Thus, the method of treatment of the present invention is useful where the conditions of edema and/or hypertension are present, and either or both of these are, or are not, also associated with a condition of hyperuricemia. The present invention will help eliminate such a hyperuricemic condition if it exists, or prevent it from occurring.

The combination indacrinone enantiomer product of the present invention can be administered to patients in a variety of therapeutic dosages and forms in conventional vehicles as, for example, by oral administration in the form of a tablet or gelatin capsule, or by intravenous injection. Also, the daily dosage of the product may be varied over the range of from 20:2.5 to 200:20 mg, (+):(−), once daily, preferably a daily dosage of from 45:5 to 90:10 mg. The dosage may be, for example, in the form of tablets containing 25, 50 or 100 mg of the active ingredient for the symptomatic adjustment of the dosage to the patient being treated.

A suitable unit dosage form for the combination indacrinone enantiomer product of the present invention can be prepared by mixing 50 mg of the enantiomer combination with 75 mg of pregelatinized starch, 75 mg of microcrystalline cellulose, and 2 mg of magnesium stearate and compressing the mixture into a tablet. Similarly, by employing more of the active ingredient and less pregelatinized starch and microcrystalline cellulose, other dosage amounts can be put up in tablets. If desired, gelatin capsules and other unit dosage forms can be prepared to incorporate the combination indacrinone enantiomer product of the present invention by conventional methods; or, said product can be made up as an injectable solution by methods well-known to pharmacists.

Another aspect of the present invention concerns two potential problems created by use of the combination indacrinone enantiomer product of the present invention: kaliuresis and urate precipitation.

It is a well-known characteristic of most potent natriuretic agents that they are also kaliuretic, that is, they cause the excretion of appreciable amounts of potassium ion. Excessive loss of potassium ion can result in hypokalemia, and this may lead to a decrease in total body potassium. Excessive potassium losses may lead to muscular weakness and a feeling of physical exhaustion, as well as other undesirable effects, such as cardiac arrhythmias.

Since excessive potassium losses may constitute an unfavorable consequence of using the combination indacrinone enantiomer product of the present invention, it is preferred to combine said product with amiloride, a potassium-sparing diuretic.

Concomitant use of amiloride will also serve to overcome a largely avoidable, though potentially more serious problem than the hypokalemia resulting from use of the combination indacrinone enantiomer product of the present invention. That problem is urate or uric acid precipitation resulting from the higher concentrations of uric acid in the urine, produced, in turn, by the uricosuric activity of the combination indacrinone enantiomer product. When such urate precipitation does occur, it can lead to uric acid crystal deposits in the urinary tract, especially in the renal tubules and the formation of bladder and kidney stones. While this potential problem is largely avoided by careful balancing of the enantiomer ratio within critical limits, where the problem does occur, it is ameliorated by concomitant administration of amiloride, which increases urinary pH by producing a lesser degree of hydrogen ion secretion. The uric acid has less of a tendency to precipitate from the less acidic urine at a given concentration. Or, put another way, the uric acid is more soluble in alkaline urine.

Amiloride, which may be named as 3,5-diamino-N-(aminoiminomethyl)-6-chloropyrazinecarboxamide, is coadministered with the combination indacrinone enantiomer product in a weight ratio range of from 5:1 to 20:1 of indacrinone enantiomer product: amiloride, provided that the total daily dosage of amiloride is from 1.25 to 10 mg. The preferred daily dosage is 5 mg., and typical preferred products are 5 mg. amiloride: 45 mg. (+):5 mg. (−) indacrinone; and 5 mg. amiloride: 90 mg. (+):10 mg. (−) indacrinone. Coadministration of the amiloride preferably takes place by utilizing a pharmaceutical dosage in which the indacrinone enantiomer and amiloride active ingredients are admixed in the required ratios.

In a further aspect of the present invention, the combination indacrinone enantiomer product of the present invention, as well as indacrinone racemic mixture, or the (+) or (−) enantiomer of indacrinone, with or without combination, additionally, with amiloride, may be combined with certain particular amino acid angiotensin converting enzyme inhibitors to give an antihypertensive product with uniquely improved properties. For example, the various indacrinone enantiomer products just referred to possess a better coincidence of duration of action alongside the duration of action of the amino acid angiotensin converting enzyme inhibitors, than does hydrochlorothiazide. This improved coincidence of activity spans gives a more therapeutically manageable product. Another advantage lies in the isouricemic or slightly hypouricemic condition obtainable with some of the various indacrinone enantiomer products. Since the use of angiotensin converting enzyme inhibitors in combination with diuretics is often recommended, it is important to avoid the hyperuricemia which usually results from the use of such diuretics, as described further above.

The particular amino acid angiotensin converting enzyme inhibitors with which the various indacrinone enantiomer products may be combined are members selected from the group consisting of (a) N-[(S)-1-(ethoxycarbonyl)-3-phenylpropyl]-L-alanyl-L-proline; (b) N-[1-(S)-carboxy-3-phenylpropyl]-L-alanine-L-proline; and (c) $N^2$-[1-(S)-carboxy-3-phenylpropyl]-L-lysyl-L-proline; and a pharmaceutically acceptable salt of the above, including the maleate salt of (a). Various other pharmaceutically acceptable salts may be employed, for example, the hydrochloride salt. The monohydrate and disulfate salts of compound (c) above have been found to be suitable.

The particular amino acid angiotensin converting enzyme inhibitors described above are administered at the rate of from 5 to 20 mg, preferably 10 to 20 mg once or twice a day, for an overall daily dosage range of from 5 to 40 mg. The inhibitors are administered at these rates together with the various indacrinone enantiomer products, optionally also together with amiloride, without any change in the dosage rates for the indacrinone enantiomer products or amiloride. The dosages for the combined indacrinone enantiomer product of the present invention, also in combination with amiloride, are described in detail above. Racemic indacrinone would be administered at the rate of from 5 to 40 mg per day; while the (+) enantiomer dosage would be 20 to 200 mg per day, and the (−) enantiomer dosage would be 2.5 to 20 mg per day.

Coadministration of the particular amino acid angiotensin converting enzyme inhibitors and various indacrinone enantiomer products, with or without amiloride, is most readily accomplished by combining the active ingredients into a suitable unit dosage form containing the proper dosages of each. Other methods of coadministration are, of course, possible.

The following example will serve to further illustrate the present invention, without, however, constituting any limitation thereof.

EXAMPLE

Tablets Containing 50 mg of Active Ingredient Per Tablet

|  | Per Tablet |
| --- | --- |
| (+) [6,7-Dichloro-2,3-dihydro-2-methyl-1-oxo-2-phenyl-1H—inden-5-yl)oxy]acetic acid | 45 mg |
| (−) [6,7-Dichloro-2,3-dihydro-2-methyl-1-oxo-2-phenyl-1H—inden-5-yl)oxy]acetic acid | 5 mg |
| Pregelatinized starch (Sta/Rx$^R$ 1500-Staley) | 75 mg |
| Microcrystalline cellulose (Abicel $^R$-FMC) | 75 mg |
| Magnesium stearate | 2 mg |

The (+) and (−)[6,7-dichloro-2,3-dihydro-2-methyl-1-oxo-2-phenyl-2H-inden-5-yl)oxy]acetic acid, pregelatinized starch, and microcrystalline cellulose are mixed well together; granulated with a 33% ethanol/water solution; dried; and milled. The magnesium stearate lubricant is then added and mixed in well, after which the mixture is compressed into a tablet.

What is claimed is:

1. A composition of matter comprising, in combination:
   (a) the (+) enantiomer of indacrinone; and
   (b) the (−) enantiomer of indacrinone;
wherein the weight ratio of (a):(b) is from about 8:1 to 10:1, that is, the (+) enantiomer is from 89% to 91% by weight of the total, and the (−) enantiomer is from 11% to 9% by weight of the total weight of indacrinone.

2. A composition according to claim 1 wherein the weight ratio of (a):(b) is 9:1, that is the (+) enantiomer is 90% by weight of the total and the (−) enantiomer is 10% by weight of the total weight of inacrinone.

3. A composition of matter comprising, in combination:
   (a) the (+) enantiomer of indacrinone; and
   (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with
   (c) amiloride;
wherein the weight ratio of (a)+(b):(C) is from 5:1 to 20:1, provided that the amount of amiloride is from 1.25 to 10 mg.

4. A pharmaceutical composition useful in the treatment of edema and hypertension which is also isouricemic or slightly hypouricemic, comprising a therapeutically effective amount of, in combination,
   (a) the (+) enantiomer of indacrinone; and
   (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with a non-toxic pharmaceutical carrier.

5. A pharmaceutical composition useful in the treatment of edema and hypertension which is also isouricemic or slightly hypouricemic, comprising a therapeutically effective amount of, in combination,
   (a) the (+) enantiomer of indacrinone; and
   (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with
   (c) amiloride;
wherein the weight ratio of (a)+(b):(c) is from 5:1 to 20:1, provided that the amount of amiloride is from 1.25 to 10 mg.; together with a non-toxic pharmaceutical carrier.

6. A method of treating edema, hypertension, and hyperuricemia, comprising the administration to a patient in need of such treatment of a therapeutically effective amount of, in combination,
   (a) the (+) enantiomer of indacrinone; and
   (b) the (−) enantiomer of indacrinone;
wherein the weight ratio of (a):(b) is from 8:1 to 10.1, that is, the (+) enantiomer is from 89% to 91% by weight of the total, and the (−) enantiomer is from 11% to 9% by weight of the total weight of indacrinone.

7. A method of treating edema, hypertension, and hyperuricemia, comprising the administration to a patient in need of such treatment of a therapeutically effective amount of, in combination,
   (a) the (+) enantiomer of indacrinone; and
   (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with
   (c) amiloride;
wherein the weight ratio of (a)+(b):(C) is from 5:1 to 20:1, provided that the amount of amiloride is from 1.25 to 10 mg.

8. A composition of matter comprising, in combination:
   (a) the (+) enantiomer of indacrinone; and
   (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with (c) a member selected from the group consisting of (1) N-[(S)-1-(ethoxycarbonyl)-3-phenylpropyl]-L-alanyl-L-proline; (2) N-[1-(S)-carboxy-3-phenylpropyl]-L-alanine-L-proline; (3) $N^2$[1-(S)-carboxy-3-phenylpropyl]-L-lysyl-L-proline; and a pharmaceutically acceptable salt of the above, including the maleate salt of (1).

9. A composition of matter comprising, in combination:
   (a) the (+) enantiomer of indacrinone; and
   (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with
   (c) amiloride;
wherein the weight ratio of (a)+(b):(C) is from 5:1 to 20:1, provided that the amount of amiloride is from 1.25 to 10 mg; and
   (d) a member selected from the group consisting of (1) N-[(S)-1-(ethoxycarbonyl)-3-phenylpropyl]-L-alanyl-L-proline; (2) N-[1-(S)-carboxy-3-phenylpropyl]-L-alanine-L-proline; (3) $N^2$[1-(S)-carboxy-3-phenylpropyl]-L-lysyl-L-proline; and a pharmaceutically acceptable salt of the above, including the maleate salt of (1).

10. A pharmaceutical composition useful in the treatment of edema and hypertension which is also isouricemic or slightly hypouricemic, comprising a therapeutically effective amount of, in combination,
    (a) the (+) enantiomer of indacrinone; and
    (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with a non-toxic pharmaceutical carrier; together with
    (c) a member selected from the group consisting of (1) N-[(S)-1-(ethoxycarbonyl)-3-phenylpropyl]-L-alanyl-L-proline; (2) N-[1(S)-carboxy-3-phenylpropyl]-L-alanine-L-proline; (3) $N^2$-[1-(S)-carboxy-3-phenylpropyl]-L-lysyl-L-proline; and a pharmaceutically acceptable salt of the above, including the maleate salt of (1).

11. A pharmaceutical composition useful in the treatment of edema and hypertension which is also isouricemic or slightly hypouricemic, comprising a therapeutically effective amount of, in combination,
    (a) the (+) enantiomer of indacrinone; and
    (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with
    (c) amiloride;
wherein the weight ratio of (a)+(b):(c) is from 5:1 to 20:1, provided that the amount of amiloride is from 1.25 to 10 mg.; together with a non-toxic pharmaceutical carrier; and
    (d) a member selected from the group consisting of (1) N-[(S)-1-(ethoxycarbonyl)-3-phenylpropyl]-L-alanyl-L-proline; (2) N-[1-(S)-carboxy-3-phenylpropyl]-L-alanine-L-proline; (3) $N^2$-[1-(S)-carboxy-3-phenylpropyl]-L-lysyl-L-proline; and a pharmaceutically acceptable salt of the above, including the maleate salt of (1).

12. A method of treating edema, hypertension, and hyperuricemia, comprising the administration to a patient in need of such treatment of a therapeutically effective amount of, in combination,
    (a) the (+) enantiomer of indacrinone; and
    (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with
    (c) a member selected from the group consisting of (1) N-[(S)-1-(ethoxycarbonyl)-3-phenylpropyl]-L-alanyl-L-proline; (2) N-[1-(S)-carboxy-3-phenylpropyl]-L-aniline-L-proline; (3) $N^2$-[1-(S)-carboxy-3-phenylpropyl]-L-lysyl-L-proline; and a pharmaceutically acceptable salt of the above, including the maleate salt of (1).

13. A method of treating edema, hypertension, and hyperuricemia, comprising the administration to a patient in need of such treatment of a therapeutically effective amount of, in combination,
    (a) the (+) enantiomer of indacrinone; and (b) the (−) enantiomer of indacrinone;
wherein the weight ratio of (a):(b) is from 8:1 to 10:1, that is, the (+) enantiomer is from 89% to 91% by weight of the total, and the (−) enantiomer is from 11% to 9% by weight of the total weight of indacrinone; together with
    (c) amiloride;
wherein the weight ratio of (a)+(b):(C) is from 5:1 to 20:1, provided that the amount of amiloride is from 1.25 to 10 mg.; and
    (d) a member selected from the group consisting of (1) N-[(S)-1-(ethoxycarbonyl)-3-phenylpropyl]-L-alanyl-L-proline; (2) N-[1-(S)-carboxy-3-phenylpropyl]-L-alanine-L-proline; (3) $N^2$[1-(S)-carboxy-3-phenylpropyl]-L-lysyl-L-proline; and a pharmaceutically acceptable salt of the above, including the maleate salt of (1).

* * * * *

UNITED STATES PATENT AND TRADEMARK OFFICE
CERTIFICATE OF CORRECTION

PATENT NO. : 4,510,322
DATED : April 9, 1985
INVENTOR(S) : Edward H. Blaine; Edward J. Cragoe, Jr.; Ralph F. Hirschmann; John F. Nancarrow, deceased; Johnathan A. Tobert It is certified that error appears in the above—identified patent and that said Letters Patent is hereby corrected as shown below:

On the title page;

Title reads:
"Indacrinone Having Enhanced Uricosuric"

Title should read:
--Indacrinone Having Enhanced Uricosuric Properties--

Signed and Sealed this

Thirteenth Day of August 1985

[SEAL]

Attest:

DONALD J. QUIGG

Attesting Officer       Acting Commissioner of Patents and Trademarks